(12) United States Patent
Montgomery

(10) Patent No.: US 7,179,453 B1
(45) Date of Patent: Feb. 20, 2007

(54) SHAVING CREAM COMPOSITION AND METHOD OF USING

(76) Inventor: Russell B. Montgomery, 1350 Brentwood Cir., Apt. D, Corona, CA (US) 92882

( * ) Notice: Subject to any disclaimer, the term of this patent is extended or adjusted under 35 U.S.C. 154(b) by 746 days.

(21) Appl. No.: 10/638,045

(22) Filed: Aug. 8, 2003

(51) Int. Cl.
*A61K 9/00* (2006.01)
*A61K 9/02* (2006.01)

(52) U.S. Cl. .................. 424/73; 424/70.1; 424/70.11; 424/70.14

(58) Field of Classification Search .............. 424/70.1, 424/70.11, 70.14, 73
See application file for complete search history.

(56) References Cited

U.S. PATENT DOCUMENTS 5,500,211 A * 3/1996 George et al. ................ 424/73

* cited by examiner

*Primary Examiner*—Michael G. Hartley
*Assistant Examiner*—Simon J. Oh

(57) ABSTRACT

A new and improved aqueous shaving cream composition and method of using the composition is disclosed. The aqueous composition comprises citric acid, hair keratin amino acids, stearic acids, boric acid, fumaric acid, SD Alcohol 40, cetyl alcohol, stearyl alcohol, calcium chloride, sodium chloride, camphor, hydroxyethylcellulose, calcium hydroxide, ammonium hydroxide, triethanolamine, gelatin, stearamidopropyl dimethylamine, methylchloroisothiazolone, methylisothiazolinone, cyclopentasiloxane, glycerin, dimeticonol, linseed oil, soybean oil, eucalyptus oil, propylene glycol, fragrance, methol, guar gum, DMDM hydantoin, sodium calcium alginate, panthenol, oleyl sarcosine, methylparaben, stearyl octyldimonium methosulfate, behenamidopropyl ethyldimonium ethosulfate, TEA-dodecylbenzenesulfonate, calcium sulfate, and disodium EDTA. The method of using the aqueous composition comprises the steps of getting, moistening, obtaining, placing, rubbing, shaving, and wiping.

5 Claims, 2 Drawing Sheets

SHAVING CREAM COMPOSITION AND METHOD OF USING

FIELD OF THE INVENTION

The present invention relates to personal hygiene products, more particularly, to a shaving cream composition and method of using the composition.

DESCRIPTION OF THE PRIOR ART

Shaving various selected areas of ones body oftentimes enhances personal hygiene and attractiveness. However, shaving does suffer a number of disadvantages such as the user may not have a comfortable shave and may even suffer scrapes and cuts. Furthermore, the razor blade may have to be discarded because the edge of the razor blade dulled prematurely.

A wide variety of shaving cream compositions is currently available on the commercial market and an even larger number of these types of devices are known in the art of shaving cream composition, for example, the shaving system for extended blade life disclosed by Fisher in U.S. Pat. No. 3,763,998; he topical delivery system and skin treatment composition employing such system disclosed by Deckner in U.S. Pat. No. 4,563,346; the topical delivery system and skin treatment compositions employing such system disclosed by Zysman et al. in U.S. Pat. No. 5,362,494; the derivatives of terpene origin, surfactant and/or fragrant composition containing them and detergent formulation based on this composition disclosed by Ricca et al. in U.S. Pat. No. 5,817,885; the shaving composition and method for preventing pseudofolliculitis barbae disclosed by Willis et al. in U.S. Pat. No. 5,853,709; and the shave gel composition disclosed by Dehan et al. in U.S. Pat. No. 5,853,710.

While all of the above-described devices fulfill their respective, particular objectives and requirements, the aforementioned patents do not describe an aqueous shaving cream composition having citric acid, hair keratin amino acids, stearic acids, boric acid, fumaric acid, SD Alcohol 40, cetyl alcohol, stearyl alcohol, calcium chloride, sodium chloride, camphor, hydroxyethylcellulose, calcium hydroxide, ammonium hydroxide, triethanolamine, gelatin, stearamidopropyl dimethylamine, methylchloroisothiazolone, methylisothiazolinone, cyclopentasiloxane, glycerin, dimeticonol, linseed oil, soybean oil, eucalyptus oil, propylene glycol, fragrance, menthol, guar gum, DMDM hydantoin, sodium calcium alginate, panthenol, oleyl sarcosine, methylparaben, stearyl octyldimonium methosulfate, behenamidopropyl ethyldimonium ethosulfate, TEA-dodecylbenzenesulfonate, calcium sulfate, and disodium EDTA. This combination of elements would specifically match the user's particular individual needs of making it possible to provide a user with a relatively smooth shave while not considerably dulling the razor blade.

Therefore, a need exists for a new and improved shaving cream composition that can be used for making it possible to provide a user with a relatively smooth shave while not considerably dulling the razor blade. In this respect, the shaving cream composition according to the present invention substantially departs from the conventional concepts and designs of the prior art, and in doing so provides an apparatus primarily developed for the purpose of providing new and improved aqueous shaving cream composition.

SUMMARY OF THE INVENTION

The present composition and method of using, according to the principles of the present invention, overcomes the shortcomings of the prior art by providing a new and improved aqueous shaving cream composition and method of using the composition is disclosed. The aqueous composition comprises citric acid, hair keratin amino acids, stearic acids, boric acid, fumaric acid, SD Alcohol 40, cetyl alcohol, stearyl alcohol, calcium chloride, sodium chloride, camphor, hydroxyethylcellulose, calcium hydroxide, ammonium hydroxide, triethanolamine, gelatin, stearamidopropyl dimethylamine, methylchloroisothiazolone, methylisothiazolinone, cyclopentasiloxane, glycerin, dimeticonol, linseed oil, soybean oil, eucalyptus oil, propylene glycol, fragrance, menthol, guar gum, DMDM hydantoin, sodium calcium alginate, panthenol, oleyl sarcosine, methylparaben, stearyl octyldimonium methosulfate, behenamidopropyl ethyldimonium ethosulfate, TEA-dodecylbenzenesulfonate, calcium sulfate, and disodium EDTA. The method of using the aqueous composition comprises the steps of getting, moistening, obtaining, placing, rubbing, shaving, and wiping.

In view of the foregoing disadvantages inherent in the known type shaving cream compositions now present in the prior art, the present invention provides an improved shaving cream composition, which will be described subsequently in great detail, is to provide a new and improved shaving cream composition which is not anticipated, rendered obvious, suggested, or even implied by the prior art, either alone or in any combination thereof.

To attain this, the present invention essentially comprises water, citric acid, hair keratin amino acids, stearic acids, boric acid, fumaric acid, SD Alcohol 40, cetyl alcohol, stearyl alcohol, calcium chloride, sodium chloride, camphor, hydroxyethylcellulose, calcium hydroxide, ammonium hydroxide, triethanolamine, gelatin, stearamidopropyl dimethylamine, methylchloroisothiazolone, methylisothiazolinone, cyclopentasiloxane, glycerin, dimeticonol, linseed oil, soybean oil, eucalyptus oil, propylene glycol, fragrance, menthol, guar gum, DMDM hydantoin, sodium calcium alginate, panthenol, oleyl sarcosine, methylparaben, stearyl octyldimonium methosulfate, behenamidopropyl ethyldimonium ethosulfate, TEA-dodecylbenzenesulfonate, calcium sulfate, and disodium EDTA.

There has thus been outlined, rather broadly, the more important features of the invention in order that the detailed description thereof that follows may be better understood, and in order that the present contribution of the art may be better appreciated.

Numerous objects, features and advantages of the present invention will be readily apparent to those of ordinary skill in the art upon reading of the following detailed description of presently preferred, but nonetheless illustrative, embodiments of the present invention when taken in conjunction with the accompany drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved shaving cream composition that has all the advantages of the prior art shaving cream composition and none of the disadvantages.

It is another object of the present invention to provide a new and improved shaving cream composition that may be easily and efficiently manufactured and marketed.

An even further object of the present invention is to provide a new and improved shaving cream composition that has a low cost of manufacture with regard to both materials and labor, and which accordingly is then susceptible of low prices of sale to the consuming public, thereby making such multipurpose storage unit and system economically available to the buying public.

Still another object of the present invention is to provide a new shaving cream composition that provides in the apparatuses and methods of the prior art some of the advantages thererof, while simultaneously overcoming some of the disadvantages normally associated therewith.

Even still another object of the present invention is to provide an aqueous shaving cream composition having citric acid, hair keratin amino acids, stearic acids, boric acid, fumaric acid, SD Alcohol 40, cetyl alcohol, stearyl alcohol, calcium chloride, sodium chloride, camphor, hydroxyethylcellulose, calcium hydroxide, ammonium hydroxide, triethanolamine, gelatin, stearamidopropyl dimethylamine, methylchloroisothiazolone, methylisothiazolinone, cyclopentasiloxane, glycerin, dimeticonol, linseed oil, soybean oil, eucalyptus oil, propylene glycol, fragrance, menthol, guar gum, DMDM hydantoin, sodium calcium alginate, panthenol, oleyl sarcosine, methylparaben, stearyl octyldimonium methosulfate, behenamidopropyl ethyldimonium ethosulfate, TEA-dodecylbenzenesulfonate, calcium sulfate, and disodium EDTA. This combination of elements makes it possible to provide a user with a relatively smooth shave while not considerably dulling the razor blade.

Lastly, it is an object of the present invention to provide a new and improved method of using the aqueous composition comprises the steps of getting, moistening, obtaining, placing, rubbing, shaving, and wiping.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompany drawings and description matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DETAILED DESCRIPTION OF THE PREFERRED EMBODIMENT

Figure 1:
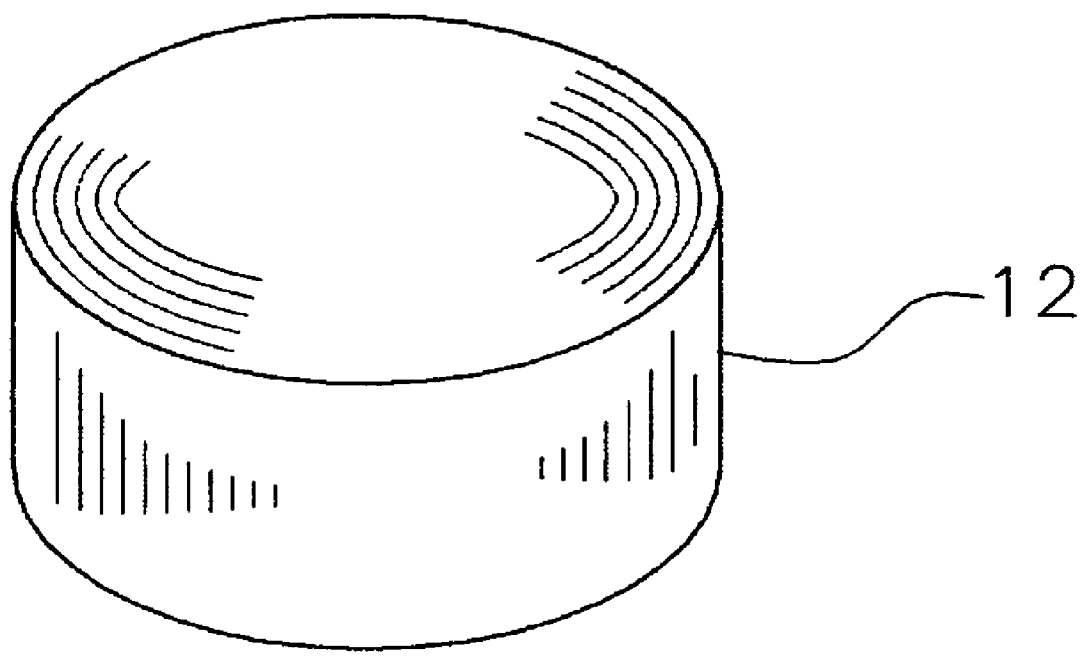
FIG. 1 is a perspective view of the cap of for a canister for containing a preferred embodiment of the shaving cream composition of the present invention.

Referring now to the drawings, and in particular FIG. 1 thereof, a cap for a canister is shown and generally designated by the reference numeral 12.

Figure 2:
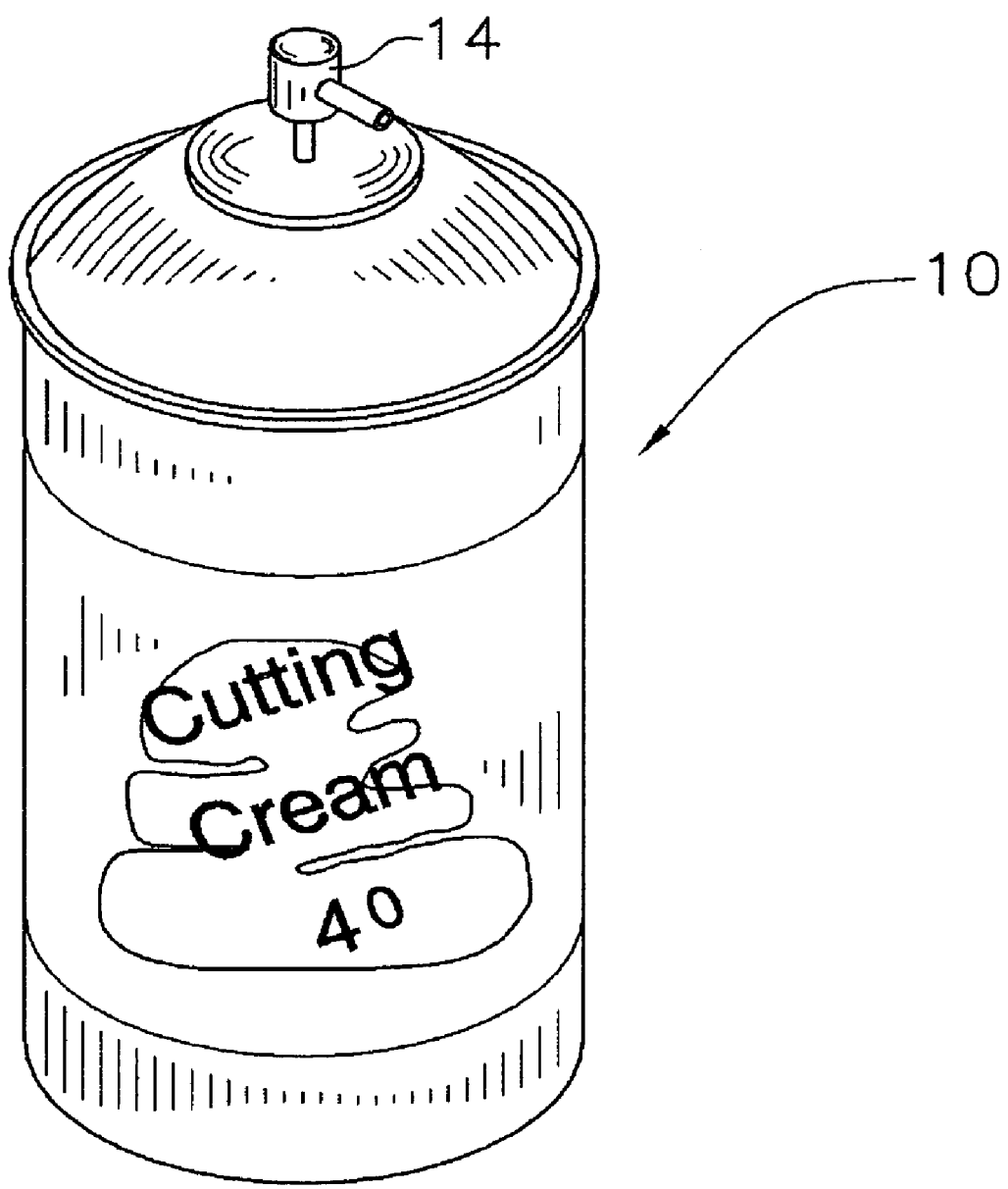
FIG. 2 is a perspective view of a canister containing a preferred embodiment of the shaving cream composition of the present invention.

Refer now to FIG. 2, which depicts a perspective view of a canister 10 containing a preferred embodiment of the shaving cream composition of the present invention. The canister 10 has an outlet nozzle 14 for ejection of the shaving cream composition.

One preferred embodiment of the aqueous based shaving cream composition comprises citric acid; hair keratin amino acids; stearic acids; boric acid; fumaric acid; SD Alcohol 40; cetyl alcohol; stearyl alcohol; calcium chloride; sodium chloride; camphor; hydroxyethylcellulose; calcium hydroxide; ammonium hydroxide; triethanolamine; gelatin; stearamidopropyl dimethylamine; methylchloroisothiazolone; methylisothiazolinone; cyclopentasiloxane; glycerin; dimeticonol; linseed oil; soybean oil; eucalyptus oil; propylene glycol; fragrance; menthol; guar gum; DMDM hydantoin; sodium calcium alginate; panthenol; oleyl sarcosine; methylparaben; stearyl octyldimonium methosulfate; behenamidopropyl ethyldimonium ethosulfate; TEA-dodecylbenzenesulfonate; calcium sulfate; and disodium EDTA.

Another preferred embodiment of the aqueous based shaving cream composition consisting essentially of citric acid in an amount of 0.3% by weight of said composition; hair keratin amino acids in an amount of 1.1% by weight of said composition; stearic acids in an amount of 0.3% by weight of said composition; boric acid in an amount of 0.3% by weight of said composition; fumaric acid in an amount of 0.3% by weight of said composition; SD Alcohol 40 in an amount of 0.5% by weight of said composition; cetyl alcohol in an amount of 0.5% by weight of said composition; stearyl alcohol in an amount of 0.5% by weight of said composition; calcium chloride in an amount of 0.5% by weight of said composition; sodium chloride in an amount 0.7% by weight of said composition; camphor in an amount of 0.5% by weight of said composition; hydroxyethylcellulose in an amount of 0.25% by weight of said composition; calcium hydroxide in an amount of 0.3% by weight of said composition; ammonium hydroxide in an amount of 0.3% by weight of said composition; triethanolamine in an amount of 0.25% by weight of said composition; gelatin in an amount of 3% by weight of said composition; stearamidopropyl dimethylamine in an amount of 0.2% by weight of said composition; methylchloroisothiazolone in an amount of 0.15% by weight of said composition; methylisothiazolinone in an amount of 0.15% by weight of said composition; cyclopentasiloxane in an amount of 1% by weight of said composition; glycerin in an amount of 2.4% by weight of said composition; dimeticonol in an amount 0.2% by weight of said composition; linseed oil in an amount of 2% by weight of said composition; soybean oil in an amount of 2% by weight of said composition; eucalyptus oil in an amount of 3% by weight of said composition; propylene glycol in an amount of 2% by weight of said composition; fragrance in an amount of 0.1% by weight of said composition; menthol is in an amount ranging of 0.6% by weight of said composition; guar gum in an amount of 0.1% by weight of said composition; DMDM hydantoin in an amount of 0.1% by weight of said composition; sodium calcium alginate in an amount of 0.1% by weight of said composition; panthenol in an amount 0.2% by weight of said composition; oleyl sarcosine in an amount 0.1% by weight of said composition; methylparaben in an amount 0.1% by weight of said composition; stearyl octyldimonium methosulfate in an amount of 0.1% by weight of said composition; behenamidopropyl ethyldimonium ethosulfate in an amount of 0.1% by weight of said composition; TEA-dodecylbenzenesulfonate in an amount of 4% by weight of said composition; calcium sulfate in an amount of 1.3% by weight of said composition; and disodium EDTA in an amount 0.2% by weight of said composition.

A preferred concentration range of the citric acid is that it is in an amount ranging from about 0.1 to 0.5% by weight of the composition with a most preferred concentration of the citric acid in an amount of 0.3% by weight of the composition.

A preferred concentration range of the hair keratin amino acids is in an amount ranging from about 0.5 to 1.5% by weight of the composition with a most preferred concentration of the hair keratin amino acids in an amount of 1.1% by weight of the composition.

A preferred concentration range of the stearic acids is in an amount ranging from about 0.1 to 0.5% by weight of the composition with a most preferred concentration of the stearic acids in an amount of 0.3% by weight of the composition.

A preferred concentration range of the boric acid is in an amount ranging from about 0.1 to 0.5% by weight of the composition with a most preferred concentration of the boric acid in an amount of 0.3% by weight of the composition.

A preferred concentration range of the fumaric acid is in an amount ranging from about 0.1 to 0.5% by weight of the composition with a most preferred concentration of the fumaric acid in an amount of 0.3% by weight of the composition.

A preferred concentration range of the SD Alcohol 40 is in an amount ranging from about 0.1 to 1.0% by weight of the composition with a most preferred concentration of the SD Alcohol 40 in an amount of 0.5% by weight of the composition. SD Alcohol 40 is ethyl alcohol that is denatured with t-butyl alcohol in combination with brucine, brucine sulfate or quessin.

A preferred concentration range of the cetyl alcohol is in an amount ranging from about 0.1 to 1.0% by weight of the composition with a most preferred concentration of the cetyl alcohol in an amount of 0.5% by weight of the composition.

A preferred concentration range of the stearyl alcohol is in an amount ranging from about 0.1 to 1.0% by weight of the composition with a most preferred concentration of the stearyl alcohol in an amount of 0.5% by weight of the composition.

A preferred concentration range of the calcium chloride is in an amount ranging from about 1.0 to 1.0% by weight of the composition with a most preferred concentration of the calcium chloride in an amount of 0.5% by weight of the composition.

A preferred concentration range of the sodium chloride is in an amount ranging from about 0.1 to 1.5% by weight of the composition with a most preferred concentration of the sodium chloride in an amount 0.7% by weight of the composition.

A preferred concentration range of the camphor is in an amount ranging from about 0.1 to 1.0% by weight of the composition with a most preferred concentration of the camphor in an amount of 0.5% by weight of the composition.

A preferred concentration range of the hydroxyethylcellulose is in an amount ranging from about 0.05 to 0.5% by weight of the composition with a most preferred concentration of the hydroxyethylcellulose in an amount of 0.25% by weight of the composition.

A preferred concentration range of the calcium hydroxide is in an amount ranging from about 0.1 to 0.5% by weight of the composition with a most preferred concentration of the calcium hydroxide in an amount of 0.3% by weight of the composition.

A preferred concentration range of the ammonium hydroxide is in an amount ranging from about 0.1 to 0.5% by weight of the composition with a most preferred concentration of the ammonium hydroxide in an amount of 0.3% by weight of the composition.

A preferred concentration range of the triethanolamine is in an amount ranging from about 0.05 to 0.4% by weight of the composition with a most preferred concentration of the triethanolamine in an amount of 0.25% by weight of the composition.

A preferred concentration range of the gelatin is in an amount ranging from about 0.1 to 0.5% by weight of the composition with a most preferred concentration of the gelatin in an amount of 3% by weight of the composition.

A preferred concentration range of the stearamidopropyl dimethylamine is in an amount ranging from about 0.1 to 0.5% by weight of the composition with a most preferred concentration of the stearamidopropyl dimethylamine in an amount of 0.2% by weight of the composition.

A preferred concentration range of the methylchloroisothiazolone is in an amount ranging from about 0.01 to 0.3% by weight of the composition with a most preferred concentration of the methylchloroisothiazolone in an amount of 0.15% by weight of the composition.

A preferred concentration range of the methylisothiazolinone is in an amount ranging from about 0.01 to 0.3% by weight of the composition with a most preferred concentration of the methylisothiazolinone in an amount of 0.15% by weight of the composition.

A preferred concentration range of the cyclopentasiloxane is in an amount ranging from about 0.1 to 2.0% by weight of the composition with a most preferred concentration of the cyclopentasiloxane in an amount of 1% by weight of the composition.

A preferred concentration range of the glycerin is in an amount ranging from about 1.0 to 5.0% by weight of the composition with a most preferred concentration of the glycerin in an amount of 2.4% by weight of the composition.

A preferred concentration range of the dimeticonol is in an amount ranging from about 0.05 to 0.4% by weight of the composition with a most preferred concentration of the dimeticonol in an amount 0.2% by weight of the composition.

A preferred concentration range of the linseed oil is in an amount ranging from about 1.0 to 5.0% by weight of the composition with a most preferred concentration of the linseed oil in an amount of 2% by weight of the composition.

A preferred concentration range of the soybean oil is in an amount ranging from about 1.0 to 5.0% by weight of the composition with a most preferred concentration of the soybean oil in an amount of 2% by weight of the composition.

A preferred concentration range of the eucalyptus oil is in an amount ranging from about 1.0 to 5.0% by weight of the composition; with a most preferred concentration of the eucalyptus oil in an amount of 3% by weight of the composition.

A preferred concentration range of the propylene glycol is in an amount ranging from about 1.0 to 3.0% by weight of the composition with a most preferred concentration of the propylene glycol in an amount of 2% by weight of the composition.

A preferred concentration range of the fragrance is in an amount ranging from about 0.01 to 1.0% by weight of the composition with a most preferred concentration of the fragrance in an amount of 0.1% by weight of the composition.

A preferred concentration range of the menthol is in an amount ranging from about 0.1 to 1.0% by weight of the composition with a most preferred concentration of the menthol is in an amount ranging of 0.6% by weight of the composition.

A preferred concentration range of the guar gum is in an amount ranging from about 0.01 to 0.05% by weight of the composition with a most preferred concentration of the guar gum in an amount of 0.1% by weight of the composition.

A preferred concentration range of the DMDM hydantoin is in an amount ranging from about 0.01 to 0.05% by weight of the composition with a most preferred concentration of the DMDM hydantoin in an amount of 0.1% by weight of the composition. DMDM hydantoin is Dimethylol dimethyl hydrantoin.

A preferred concentration range of the sodium calcium alginate is in an amount ranging from about 0.01 to 0.05% by weight of the composition with a most preferred concentration of the sodium calcium alginate in an amount of 0.1% by weight of the composition.

A preferred concentration range of the panthenol is in an amount ranging from about 0.05 to 0.4% by weight of the composition with a most preferred concentration of the panthenol in an amount 0.2% by weight of the composition.

A preferred concentration range of the oleyl sarcosine is in an amount ranging from about 0.01 to 0.3% by weight of the composition with a most preferred concentration of the oleyl sarcosine in an amount 0.1% by weight of the composition.

A preferred concentration range of the methylparaben is in an amount ranging from about 0.01 to 0.3% by weight of the composition with a most preferred concentration of the methylparaben in an amount 0.1% by weight of the composition.

A preferred concentration range of the stearyl octyldimonium methosulfate is in an amount ranging from about 0.01 to 0.3% by weight of the composition with a most preferred concentration of the stearyl octyldimonium methosulfate in an amount of 0.1% by weight of the composition.

A preferred concentration range of the behenamidopropyl ethyldimonium ethosulfate is in an amount ranging from about 0.01 to 0.3% by weight of the composition with a most preferred concentration of the behenamidopropyl ethyldimonium ethosulfate in an amount of 0.1% by weight of the composition.

A preferred concentration range of the TEA-dodecylbenzenesulfonate is in an amount ranging from about 1.0 to 7.0% by weight of the composition with a most preferred concentration of the TEA-dodecylbenzenesulfonate in an amount of 4% by weight of the composition. TEA is triethanolamine.

A preferred concentration range of the calcium sulfate is in an amount ranging from about 0.6 to 2.0% by weight of the composition with a most preferred concentration of the calcium sulfate in an amount of 1.3% by weight of the composition.

A preferred concentration range of the disodium EDTA is in an amount ranging from about 0.05 to 0.5% by weight of the composition with a most preferred concentration of the disodium EDTA in an amount 0.2% by weight of the composition.

One preferred embodiment of the method of using an aqueous based shaving cream composition for use is shaving, the method comprises the steps of getting, moistening, obtaining, placing, rubbing, shaving, and wiping. The obtaining step comprises obtaining the aqueous based shaving cream composition consisting essentially of citric acid in an amount of 0.3% by weight of the composition; hair keratin amino acids in an amount of 1.1% by weight of the composition; stearic acids in an amount of 0.3% by weight of the composition; boric acid in an amount of 0.3% by weight of the composition; fumaric acid in an amount of 0.3% by weight of the composition; SD Alcohol 40 in an amount of 0.5% by weight of the composition; cetyl alcohol in an amount of 0.5% by weight of the composition; stearyl alcohol in an amount of 0.5% by weight of the composition; calcium chloride in an amount of 0.5% by weight of the composition; sodium chloride in an amount 0.7% by weight of the composition; camphor in an amount of 0.5% by weight of the composition; hydroxyethylcellulose in an amount of 0.25% by weight of the composition; calcium hydroxide in an amount of 0.3% by weight of the composition; ammonium hydroxide in an amount of 0.3% by weight of the composition; triethanolamine in an amount of 0.25% by weight of the composition; gelatin in an amount of 3% by weight of the composition; stearamidopropyl dimethylamine in an amount of 0.2% by weight of the composition; methylchloroisothiazolone in an amount of 0.15% by weight of the composition; methylisothiazolinone in an amount of 0.15% by weight of the composition; cyclopentasiloxane in an amount of 1% by weight of the composition; glycerin in an amount of 2.4% by weight of the composition; dimeticonol in an amount 0.2% by weight of the composition; linseed oil in an amount of 2% by weight of the composition; soybean oil in an amount of 2% by weight of the composition; eucalyptus oil in an amount of 3% by weight of the composition; propylene glycol in an amount of 2% by weight of the composition; fragrance in an amount of 0.1% by weight of the composition; menthol is in an amount ranging of 0.6% by weight of the composition; guar gum in an amount of 0.1% by weight of the composition; DMDM hydantoin in an amount of 0.1% by weight of the composition; sodium calcium alginate in an amount of 0.1% by weight of the composition; panthenol in an amount 0.2% by weight of the composition; oleyl sarcosine in an amount 0.1% by weight of the composition; methylparaben in an amount 0.1% by weight of the composition; stearyl octyldimonium methosulfate in an amount of 0.1% by weight of the composition; behenamidopropyl ethyldimonium ethosulfate in an amount of 0.1% by weight of the composition; TEA-dodecylbenzenesulfonate in an amount of 4% by weight of the composition; calcium sulfate in an amount of 1.3% by weight of the composition; and disodium EDTA in an amount 0.2% by weight of the composition. The placing step comprises placing an aliquot of the composition onto a portion of a user's hand, the placing step performed subsequent to the obtaining step. The rubbing step comprises rubbing the aliquot of the composition onto a portion of the user's legs, the rubbing step performed subsequent to the placing step. The getting step comprises getting a razor blade. The shaving step comprises shaving any excess hair from the portion of the user's legs with the razor blade when the aliquot is rubbed onto the portion of the user's legs, the shaving step performed subsequent to the getting and rubbing steps. The moistening step comprises moistening a towel with warm water. The wiping step comprises wiping off any residual amount of the aliquot rubbed onto the portion of the user's legs with the moistened towel, the wiping step performed subsequent to the shaving and moistening steps.

As to the manner of usage and operation of the present invention, the same should be apparent from the above description. Accordingly, no further discussion relating to the manner of usage and operation will be provided.

While a preferred embodiment of the shaving cream composition has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

With respect to the above description then, it is to be realized that the optimum dimensional relationships for the parts of the invention, to include variations in size materials, shape, form, function and manner of operation, assembly and use, are deemed readily apparent and obvious to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes or variations, thereof, or the them "having" or variations, thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combination any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An aqueous based shaving cream composition for use in shaving, said composition comprising: citric acid; hair keratin amino acids; stearic acids; boric acid; fumaric acid; SD Alcohol 40; cetyl alcohol; stearyl alcohol; calcium chloride; sodium chloride; camphor; hydroxyethylcellulose; calcium hydroxide; ammonium hydroxide; triethanolamine; gelatin; stearamidopropyl dimethylamine; methylchloroisothiazolone; methylisothiazolinone; cyclopentasiloxane; glycerin; dimeticonol; linseed oil; soybean oil; eucalyptus oil; propylene glycol; fragrance; menthol; guar gum; DMDM hydantoin; sodium calcium alginate; panthenol; oleyl sarcosine; methylparaben; stearyl octyldimonium methosulfate; behenamidopropyl ethyldimonium ethosulfate; TEA-dodecylbenzenesulfonate; calcium sulfate; and disodium EDTA.

2. The composition described in claim 1 wherein said citric acid is in an amount ranging from about 0.1 to 0.5% by weight of said composition; said hair keratin amino acids is in an amount ranging from about 0.5 to 1.5% by weight of said composition; said stearic acids is in an amount ranging from about 0.1 to 0.5% by weight of said composition; said boric acid is in an amount ranging from about 0.1 to 0.5% by weight of said composition; said fumaric acid is in an amount ranging from about 0.1 to 0.5% by weight of said composition; said SD Alcohol 40 is in an amount ranging from about 0.1 to 1.0% by weight of said composition; said cetyl alcohol is in an amount ranging from about 0.1 to 1.0% by weight of said composition; said stearyl alcohol is in an amount ranging from about 0.1 to 1.0% by weight of said composition; said calcium chloride is in an amount ranging from about 1.0 to 1.0% by weight of said composition; said sodium chloride is in an amount ranging from about 0.1 to 1.5% by weight of said composition; said camphor is in an amount ranging from about 0.1 to 1.0% by weight of said composition; said hydroxyethylcellulose is in an amount ranging from about 0.05 to 0.5% by weight of said composition; said calcium hydroxide is in an amount ranging from about 0.1 to 0.5% by weight of said composition; said ammonium hydroxide is in an amount ranging from about 0.1 to 0.5% by weight of said composition; said triethanolamine is in an amount ranging from about 0.05 to 0.4% by weight of said composition; said gelatin is in an amount ranging from about 0.1 to 0.5% by weight of said composition; said stearamidopropyl dimethylamine is in an amount ranging from about 0.1 to 0.5% by weight of said composition; said methylchloroisothiazolone is in an amount ranging from about 0.01 to 0.3% by weight of said composition; said methylisothiazolinone is in an amount ranging from about 0.01 to 0.3% by weight of said composition; said cyclopentasiloxane is in an amount ranging from about 0.1 to 2.0% by weight of said composition; said glycerin is in an amount ranging from about 1.0 to 5.0% by weight of said composition; said dimeticonol is in an amount ranging from about 0.05 to 0.4% by weight of said composition; said linseed oil is in an amount ranging from about 1.0 to 5.0% by weight of said composition; said soybean oil is in an amount ranging from about 1.0 to 5.0% by weight of said composition; said eucalyptus oil is in an amount ranging from about 1.0 to 5.0% by weight of said composition; said propylene glycol is in an amount ranging from about 1.0 to 3.0% by weight of said composition; said fragrance is in an amount ranging from about 0.01 to 1.0% by weight of said composition; said menthol is in an amount ranging from about 0.1 to 1.0% by weight of said composition; said guar gum is in an amount ranging from about 0.01 to 0.05% by weight of said composition; said DMDM hydantoin is in an amount ranging from about 0.01 to 0.05% by weight of said composition; said sodium calcium alginate is in an amount ranging from about 0.01 to 0.05% by weight of said composition; said panthenol is in an amount ranging from about 0.05 to 0.4% by weight of said composition; said oleyl sarcosine is in an amount ranging from about 0.01 to 0.3% by weight of said composition; said methylparaben is in an amount ranging from about 0.01 to 0.3% by weight of said composition; said stearyl octyldimonium methosulfate is in an amount ranging from about 0.01 to 0.3% by weight of said composition; said behenamidopropyl ethyldimonium ethosulfate is in an amount ranging from about 0.01 to 0.3% by weight of said composition; said TEA-dodecylbenzenesulfonate is in an amount ranging from about 1.0 to 7.0% by weight of said composition; said calcium sulfate is in an amount ranging from about 0.6 to 2.0% by weight of said composition; and said disodium EDTA is in an amount ranging from about 0.05 to 0.5% by weight of said composition.

3. The composition described in claim 1 wherein said citric acid in an amount of 0.3% by weight of said composition; said hair keratin amino acids in an amount of 1.1% by weight of said composition; said stearic acids in an amount of 0.3% by weight of said composition; said boric acid in an amount of 0.3% by weight of said composition; said fumaric acid in an amount of 0.3% by weight of said composition; said SD Alcohol 40 in an amount of 0.5% by weight of said composition; said cetyl alcohol in an amount of 0.5% by weight of said composition; said stearyl alcohol in an amount of 0.5% by weight of said composition; said calcium chloride in an amount of 0.5% by weight of said composition; said sodium chloride in an amount 0.7% by weight of said composition; said camphor in an amount of 0.5% by weight of said composition; said hydroxyethylcellulose in an amount of 0.25% by weight of said composition; said calcium hydroxide in an amount of 0.3% by weight of said composition; said ammonium hydroxide in an amount of 0.3% by weight of said composition; said triethanolamine in an amount of 0.25% by weight of said composition; said gelatin in an amount of 3% by weight of said composition; said stearamidopropyl dimethylamine in an amount of 0.2% by weight of said composition; said methylchloroisothiazolone in an amount of 0.15% by weight of said composition; said methylisothiazolinone in an amount of 0.15% by weight of said composition; said cyclopentasiloxane in an amount of 1% by weight of said composition; said glycerin in an amount of 2.4% by weight of said composition; said dimeticonol in an amount 0.2% by weight of said composition; said linseed oil in an amount of 2% by weight of said composition; said soybean oil in an amount of 2% by weight of said composition; said eucalyptus oil in an amount of 3% by weight of said composition; said propylene glycol in an amount of 2% by weight of said composition; said fragrance in an amount of 0.1% by weight of said composition; said menthol is in an amount ranging of 0.6% by weight of said composition; said guar gum in an amount of 0.1% by weight of said composition; said DMDM hydantoin in an amount of 0.1% by weight of said composition; said sodium calcium alginate in an amount of 0.1% by weight of said composition; said panthenol in an amount 0.2% by weight of said composition; said oleyl sarcosine in an amount 0.1% by weight of said composition; said methylparaben in an amount 0.1% by weight of said composition; said stearyl octyldimonium methosulfate in an amount of 0.1% by weight of said composition; said behenamidopropyl ethyldimonium ethosulfate in an amount of 0.1% by weight of said composition; said TEA-dodecylbenzenesulfonate in an amount of 4% by weight of said composition; said calcium sulfate in an amount of 1.3% by weight of said composition; and said disodium EDTA in an amount 0.2% by weight of said composition.

4. An aqueous based shaving cream composition for use in shaving, said composition consisting essentially of citric acid in an amount of 0.3% by weight of said composition; hair keratin amino acids in an amount of 1.1% by weight of said composition; stearic acids in an amount of 0.3% by weight of said composition; boric acid in an amount of 0.3% by weight of said composition; fumaric acid in an amount of 0.3% by weight of said composition; SD Alcohol 40 in an amount of 0.5% by weight of said composition; cetyl alcohol in an amount of 0.5% by weight of said composition; stearyl alcohol in an amount of 0.5% by weight of said composition; calcium chloride in an amount of 0.5% by weight of said composition; sodium chloride in an amount 0.7% by weight of said composition; camphor in an amount of 0.5% by weight of said composition; hydroxyethylcellulose in an amount of 0.25% by weight of said composition; calcium hydroxide in an amount of 0.3% by weight of said composition; ammonium hydroxide in an amount of 0.3% by weight of said composition; triethanolamine in an amount of 0.25% by weight of said composition; gelatin in an amount of 3% by weight of said composition; stearamidopropyl dimethylamine in an amount of 0.2% by weight of said composition; methylchloroisothiazolone in an amount of 0.15% by weight of said composition; methylisothiazolinone in an amount of 0.15% by weight of said composition; cyclopentasiloxane in an amount of 1% by weight of said composition; glycerin in an amount of 2.4% by weight of said composition; dimeticonol in an amount 0.2% by weight of said composition; linseed oil in an amount of 2% by weight of said composition; soybean oil in an amount of 2% by weight of said composition; eucalyptus oil in an amount of 3% by weight of said composition; propylene glycol in an amount of 2% by weight of said composition; fragrance in an amount of 0.1% by weight of said composition; menthol is in an amount ranging of 0.6% by weight of said composition; guar gum in an amount of 0.1% by weight of said composition; DMDM hydantoin in an amount of 0.1% by weight of said composition; sodium calcium alginate in an amount of 0.1% by weight of said composition; panthenol in an amount 0.2% by weight of said composition; oleyl sarcosine in an amount 0.1% by weight of said composition; methylparaben in an amount 0.1% by weight of said composition; stearyl octyldimonium methosulfate in an amount of 0.1% by weight of said composition; behenamidopropyl ethyldimonium ethosulfate in an amount of 0.1% by weight of said composition; TEA-dodecylbenzenesulfonate in an amount of 4% by weight of said composition; calcium sulfate in an amount of 1.3% by weight of said composition; and disodium EDTA in an amount 0.2% by weight of said composition.

5. A method of using an aqueous based shaving cream composition for use in shaving, said method comprising:
obtaining the aqueous based shaving cream composition consisting essentially of citric acid in an amount of 0.3% by weight of said composition; hair keratin amino acids in an amount of 1.1% by weight of said composition; stearic acids in an amount of 0.3% by weight of said composition; boric acid in an amount of 0.3% by weight of said composition; fumaric acid in an amount of 0.3% by weight of said composition; SD Alcohol 40 in an amount of 0.5% by weight of said composition; cetyl alcohol in an amount of 0.5% by weight of said composition; stearyl alcohol in an amount of 0.5% by weight of said composition; calcium chloride in an amount of 0.5% by weight of said composition; sodium chloride in an amount 0.7% by weight of said composition; camphor in an amount of 0.5% by weight of said composition; hydroxyethylcellulose in an amount of 0.25% by weight of said composition; calcium hydroxide in an amount of 0.3% by weight of said composition; ammonium hydroxide in an amount of 0.3% by weight of said composition; triethanolamine in an amount of 0.25% by weight of said composition; gelatin in an amount of 3% by weight of said composition; stearamidopropyl dimethylamine in an amount of 0.2% by weight of said composition; methylchloroisothiazolone in an amount of 0.15% by weight of said composition; methylisothiazolinone in an amount of 0.15% by weight of said composition; cyclopentasiloxane in an amount of 1% by weight of said composition; glycerin in an amount of 2.4% by weight of said composition; dimeticonol in an amount 0.2% by weight of said composition; linseed oil in an amount of 2% by weight of said composition; soybean oil in an amount of 2% by weight of said composition; eucalyptus oil in an amount of 3% by weight of said composition; propylene glycol in an amount of 2% by weight of said composition; fragrance in an amount of 0.1% by weight of said composition; menthol is in an amount ranging of 0.6% by weight of said composition; guar gum in an amount of 0.1% by weight of said composition; DMDM hydantoin in an amount of 0.1% by weight of said composition; sodium calcium alginate in an amount of 0.1% by weight of said composition; panthenol in an amount 0.2% by weight of said composition; oleyl sarcosine in an amount 0.1% by weight of said composition; methylparaben in an amount 0.1% by weight of said composition; stearyl octyldimonium methosulfate in an amount of 0.1% by weight of said composition; behenamidopropyl ethyldimonium ethosulfate in an amount of 0.1% by weight of said composition; TEA-dodecylbenzenesulfonate in an amount of 4% by weight of said composition; calcium sulfate in an amount of 1.3% by weight of said composition; and disodium EDTA in an amount 0.2% by weight of said composition;

placing an aliquot of the composition onto a portion of a user's hand, said placing step performed subsequent to said obtaining step;

rubbing the aliquot of the composition onto a portion of the user's legs, said rubbing step performed subsequent to said placing step;

obtaining a razor blade;

shaving any excess hair from the portion of the user's legs with the razor blade when the aliquot is rubbed onto the portion of the user's legs, said shaving step performed subsequent to said getting and rubbing steps;

moistening a towel with warm water; and wiping off any residual amount of the aliquot rubbed onto the portion of the user's legs with the moistened towel, said wiping step performed subsequent to said shaving and moistening steps.

* * * * *